(12) United States Patent
Pavageau et al.

(10) Patent No.: US 8,318,871 B2
(45) Date of Patent: *Nov. 27, 2012

(54) PROCESS FOR PREPARING A POLYMER

(75) Inventors: Bertrand Pavageau, Villenave d'Ornon (FR); Galder Cristobal, Shanghai (CN); Rabih Rached, Millery (FR); Chi-Thanh Vuong, Lognes (FR)

(73) Assignee: Rhodia Operations, Aubervilliers (FR)

( * ) Notice: Subject to any disclaimer, the term of this patent is extended or adjusted under 35 U.S.C. 154(b) by 331 days.

This patent is subject to a terminal disclaimer.

(21) Appl. No.: 12/445,391

(22) PCT Filed: Oct. 15, 2007

(86) PCT No.: PCT/EP2007/060985
§ 371 (c)(1),
(2), (4) Date: Feb. 4, 2010

(87) PCT Pub. No.: WO2008/043860
PCT Pub. Date: Apr. 17, 2008

(65) Prior Publication Data
US 2010/0152395 A1    Jun. 17, 2010

(30) Foreign Application Priority Data

Oct. 13, 2006 (FR) ..................... 06 08991

(51) Int. Cl.
*C08F 2/00* (2006.01)
*G01N 35/08* (2006.01)
*G01N 15/06* (2006.01)
*B01J 19/18* (2006.01)

(52) U.S. Cl. ........... 526/64; 526/227; 436/52; 422/68.1; 422/132

(58) Field of Classification Search ............ 526/64, 526/227; 436/52; 422/68.1, 132
See application file for complete search history.

(56) References Cited

U.S. PATENT DOCUMENTS 3,480,596 A * 11/1969 Simons ............ 528/335
2010/0129917 A1 * 5/2010 Panizza et al. ............ 436/52

* cited by examiner

*Primary Examiner* — William Cheung
(74) *Attorney, Agent, or Firm* — SNR Denton US LLP

(57) ABSTRACT

The present invention relates to a process which comprises preparing polymers. The process uses an appropriate installation, and may comprise determining at least one parameter of a physical and/or chemical conversion. The invention also relates to a corresponding screening process. According to this process, a polymerization reaction medium is made to flow in a tubular flow member.

36 Claims, 7 Drawing Sheets

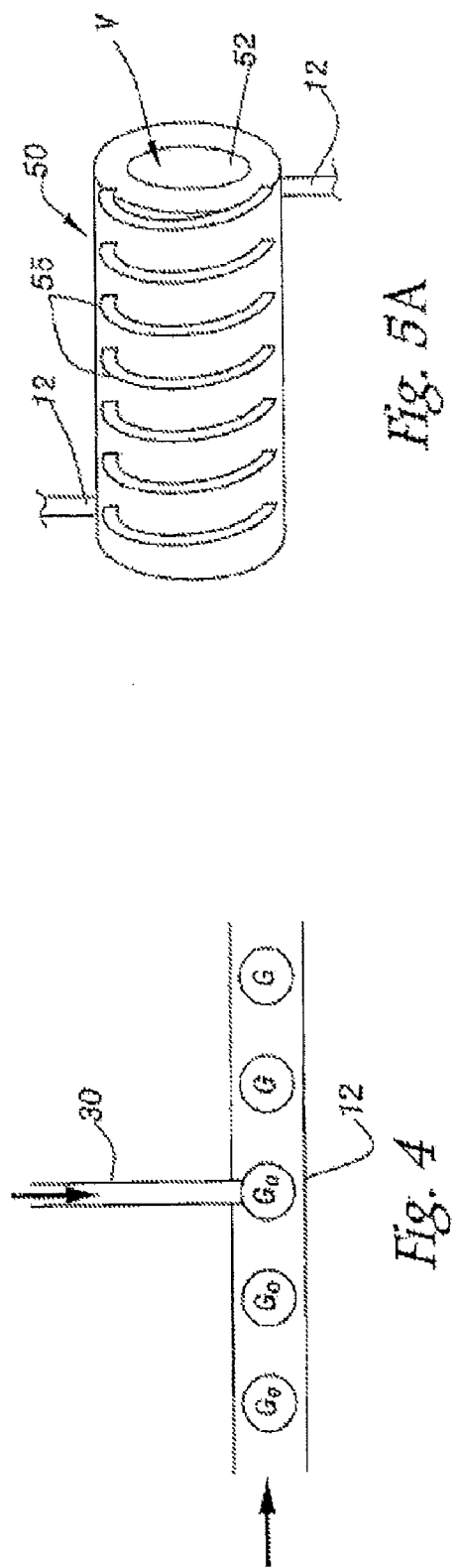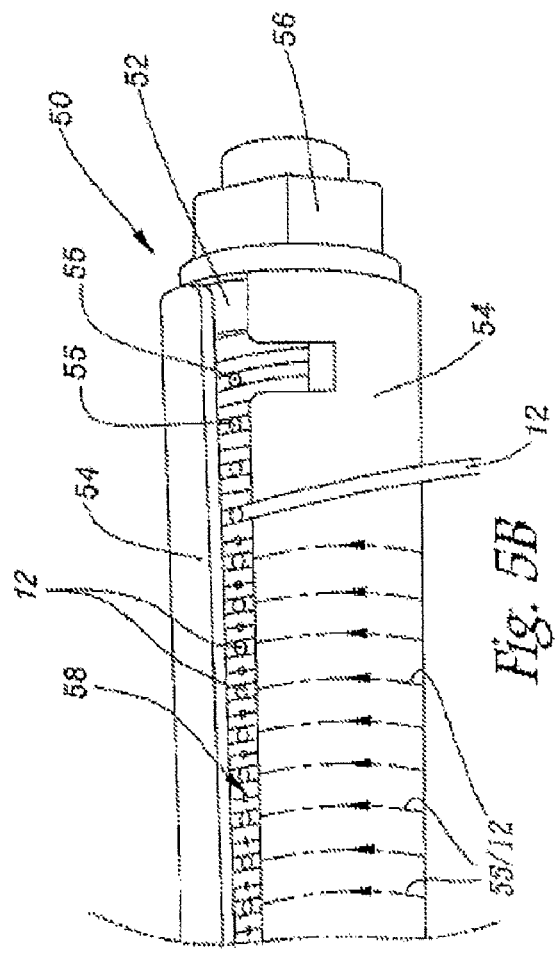

PROCESS FOR PREPARING A POLYMER

The present invention relates to a process comprising a preparation of polymers. The process uses an appropriate installation, and may comprise a determination of at least one parameter of a physical and/or chemical conversion. The invention also relates to a corresponding screening process.

Generally, the expression "physical and/or chemical conversion" is understood to mean any type of interaction capable of taking place in a mixture of at least two components. In a non-limiting manner, this conversion may be a reaction of chemical and/or physical type, such as for example any type of conventional chemical reaction, especially polymerization reactions, and also a crystallization or a precipitation, a gelification, or else inter alia a modification of a liquid/vapor equilibrium. Generally, in the sense of the invention, such a conversion is capable of making use of chemical mechanisms, by exchange or joining of electrons, physical interactions or repulsions, such as hydrogen bonds, electrostatic interactions, steric attractions or repulsions, affinities for various hydrophilic and/or hydrophobic media, formulation stabilities, flocculations or else phase transfers, for example of liquid/liquid, solid/liquid or gas/liquid type.

In the sense of the invention, the parameters of such a conversion are, in a non-limiting manner, the chemical reaction kinetics in homogeneous or heterogeneous medium, the conditions for obtaining an optimum yield for chemical reactions, reaction enthalpies, temporal processes of chemical and physical reactions, and also solubility or even phase diagrams.

The polymers are products obtained by chemical conversion from monomers, where appropriate in the presence of other compounds such as catalysts, reaction media such as solvents (in the context of solution polymerizations), or dispersion media (in the context of emulsion or suspension polymerizations for example). The chemical conversion from monomers is polymerization. It may be accompanied by physical or physicochemical conversions such as phase changes, precipitations, gelling, etc.

The determination of the parameters of a conversion is already used, owing to the technique of microfluidic type flow.

These microfluidic flows are, for example, described in M. Madou "Fundamentals of Microfabrication: The Science of Miniaturization", CRC Press. (1997). They take advantage of mechanical systems for which the micron-scale and/or nano-scale sizes allow the handling of very small volumes of fluid. This miniaturization, coupled with the use of appropriate analysis techniques, opens the way to numerous applications in fields as diverse as biology, analytical chemistry, chemical engineering or physics.

Thus, this technique makes it possible to envisage, for example, a set of chemical processes on a chip, so as to recreate a laboratory on a particularly limited area of around a few cm², that is to say the "Lab-on-Chip": see, in particular, J. Knight, Nature, 418, 474 (2002). Such a miniaturization thus offers significant prospects in the field of chemical engineering, with a view to increasing the selectivity and also the yield of the reactions implemented.

The use of plugs, in particular drops, in the microfluidic domain proves very promising. This is because these drops, the volume of which is extremely low, typically between a picoliter and nanoliter, make it possible to carry out chemical reactions within them. This is described, for example, in B. Zheng, L. S. Roach, R. Ismagilov, J. Am. Chem. Soc 125, 11170 (2003). Furthermore, microfluidic production techniques allow the formation of monodisperse drops with a constant production frequency.

Consequently the drops, which thus form nano-reactors, flow at a constant speed, so that there is an equivalence between the distance traveled and the reaction time. In other words, a drop situated at a given location of the fluidic flow network is representative of the reaction studied at a given instant. By combining conventional analysis techniques, of Raman, infrared, visible or fluorescent type, it is then possible to monitor the kinetics of a reaction and to adjust the composition of the drops, in order to very rapidly target the optimal chemical reaction conditions, while only using very low volumes of reactants.

Even though the microfluidic type techniques have numerous advantages, such as those mentioned above, they involve, however, certain drawbacks. Specifically, they are accompanied by a relatively high production cost, linked in particular to the use of the soft lithography technique. Furthermore, the microfluidic flow devices are not readily adjustable. Finally, the microfluidic technique does not allow a satisfactory study of certain types of reaction.

Furthermore, generally, there is a constant need for the industry to develop novel products, having novel properties, in particular novel polymers or novel compositions comprising novel polymers and/or novel combinations of chemicals comprising at least one polymer. The physical and/or chemical conversions that use polymers or polymerizations have significant properties for a good number of applications, which it is very often advisable to test in Research and Development procedures. There is a need for processes and installations for accelerating the Research and Development procedures, for example for testing a larger number of products and/or for carrying out tests on smaller amounts of products, and/or for carrying out the tests more rapidly, and/or carrying out tests that relate to conversions that are too slow to be studied in the devices from the prior art mentioned above.

This being stated, the invention aims to provide a process for determining a parameter of a conversion which, while overall allowing the same possibilities as the microfluidic technique, substantially overcomes the drawbacks linked to the latter.

For this purpose, one subject of the invention is a process comprising a preparation of polymers, in which a polymerization reaction medium, preferably a radical polymerization reaction medium, is made to flow in a tubular flow member (12; 112), known as a downstream tubular flow member, said medium being continuous or being composed of a succession of plugs (G; G') in a carrier phase (P), and optionally one of the following operations:
- at least one analysis of the reaction medium, preferably of at least one plug, is carried out and at least one physical and/or chemical conversion feature of the polymer and/or of the polymerization is deduced therefrom;
- the reaction medium is recovered, the polymer is optionally isolated and used; and/or
- the polymer is tested.

According to other features of the invention:
- the physicochemical system is formed from at least two components and these two components are circulated in at least two upstream tubular flow members, which open into the downstream tubular flow member;
- the or each tubular flow member has an equivalent diameter between 10 micrometers and 50 mm, preferably between 50 micrometers and 5 mm, more preferably between 100 micrometers and 1 mm;
- said at least two components are mixed in a mixing zone substantially at the same time as these components are brought into contact with the carrier phase, in a contacting zone substantially merged with the mixing zone;

said at least two upstream flow members and the downstream flow member are concentric;

the contacting zone is located immediately downstream of an overlap zone between the downstream flow member and the outer upstream flow member;

the conversion that takes place in the plugs is stopped, especially by means of a quench, and at least one off-line analysis is carried out, especially in a chromatograph;

a beam from an analysis unit, for example of RAMAN type, is pointed toward one zone of the downstream tubular flow member in which the conversion continues to take place;

the beam is pointed toward one and the same location of the downstream tubular flow member, and an analysis of several plugs that flow successively past said location is carried out;

at least one part of the downstream flow member is placed in a member for maintaining at a given temperature;

it immobilizes, in the downstream flow member, at least some plugs, which enables the conversion to be followed without displacement of these plugs, then these plugs are again made to flow in this downstream tubular member after observation of this latent period;

primary plugs, especially comprising a first monomer and a polymerization initiator, are made to flow in the tubular flow member, and added to each primary plug is at least one other component, especially another monomer and/or a supplementary amount of an initiator, so as to form definitive plugs;

the plugs are made to flow in the downstream tubular flow member at a throughput between 1 ml/h and 1000 ml/h, preferably between 5 and 100 ml/h;

the length of the downstream tubular flow member is between 50 cm and 10 m, in particular between 1 and 4 m;

the parameter that is deduced is a rate of progress of the conversion, for example kinetics for disappearance of reactive products, kinetics for appearance of products resulting from a main reaction, or else kinetics for production of by-products to this main reaction;

the composition of several plugs and/or the temperature of the maintaining member is programmed by computer means and/or the results of the various analyses are acquired by said computer means.

Another subject of the invention is a device for determining at least one parameter of a physical and/or chemical conversion, comprising:

a tubular flow member, known as a downstream tubular flow member, the equivalent diameter of which is between 10 micrometers and 50 mm, preferably between 50 micrometers and 5 mm, more preferably between 100 micrometers and 1 mm;

means for generating a succession of plugs separated by a carrier phase in this downstream tubular flow member;

means for analyzing these plugs; and means for determining the or each parameter.

According to other features of the invention:

the downstream tubular flow member is connected to means that make it possible to stop said physical and/or chemical conversion of the polymer and/or polymerization, especially by means of a quench, and this downstream tubular flow member then leads to an external analyzer, especially of chromatograph type;

the analysis means comprise an analysis unit, for example of RAMAN type, having a beam suitable for being pointed toward the downstream tubular flow member;

the means for generating plugs comprise at least one upstream tubular flow member, each of which is suitable for supplying a component of the reaction medium, the or each upstream tubular flow member opening into the downstream tubular flow member, the generating means also comprising a means for conveying the carrier phase, that also opens into the downstream tubular flow member;

at least two upstream tubular flow members are provided which have downstream ends that define a mixing zone for the components of the plugs, these downstream ends opening into the downstream tubular flow member in a contacting zone substantially merged with the mixing zone;

the length of the downstream tubular flow member is between 50 cm and 10 m, in particular between 1 and 4 m;

this device also comprises a member for maintaining at a given temperature, in the vicinity of which at least one part of the downstream tubular flow member extends;

the member for maintaining at a given temperature comprises a hollow body, that defines an internal volume for receiving a heat transfer fluid, this internal volume being bordered by a wall at the periphery of which said part of the downstream tubular flow member extends;

the wall is hollowed out by at least one series of peripheral grooves, each series of grooves making it possible to receive a downstream tubular flow member of corresponding transverse dimension;

the part of the downstream tubular flow member placed around the wall is covered by a peripheral flange, in which an analysis unit viewing window is made.

The final subject of the invention is a process for screening several polymer preparations, in which several different polymerizations are carried out, by modifying the reaction medium and/or the operating conditions, the analysis and/or the test is carried out according to the process as above and at least one preferred polymer is identified.

In the present invention, a reaction medium flows into the downstream flow member. The reaction medium is a polymerization medium, preferably a medium for radical polymerization, from monomers, and optionally other compounds, for example a catalyst or an initiator. The reaction medium may comprise a solvent for the monomers and/or for the polymer or a liquid for dispersing (in the form of an emulsion or of a solid dispersion) the monomers and/or the polymer.

According to one embodiment, the reaction medium is composed of a succession of plugs in a carrier phase (P). In this embodiment, at a given point of the flow member, a plug of reaction medium and a plug of carrier phase pass successively and distinctively. No polymerization takes place in the carrier phase (P). The latter makes it possible to transport the small reaction media that are constituted by the plugs and to separate them. It is noted that each plug, by way of reaction medium, may be in the form of a solution, emulsion or dispersion type reaction medium. It is possible, for example, to have a plug in the form itself of a solution or of a direct or inverse emulsion or of a dispersion, then carrier phase, then another plug in an identical form to the preceding form. The set of plugs, and the carrier phase, the characteristic sizes of which are of the same order, is not considered itself to be an emulsion of plugs in the carrier phase or of the carrier phase in the medium constituted by the plugs, of the same type as the emulsions conventionally used in the field of polymerization. As explained above on the other hand, it is not excluded that each of the plugs constitutes, individually, an emulsion of the same type as the emulsions conventionally used in the field of polymerization.

According to another embodiment, the reaction medium is continuous. The term "continuous" is understood to mean that it is not composed of a succession of plugs in a carrier phase. In this embodiment, at a given point of the flow member, the reaction medium flows continuously, without maintaining a succession of plugs and of carrier phase. The continuous medium is understood in contrast with the embodiment given above. In the context of the implementation of the embodiment referred to as the continuous embodiment, it is not excluded that the reaction medium is in the form of an emulsion or of a dispersion of the same types as the emulsions or dispersions conventionally used in the field of polymerization. These may be, for example, polymerizations in direct emulsion or in inverse emulsion. It is also possible to use polymerizations in solution.

The reaction medium is a polymerization medium, for polymerization from monomers. The polymers prepared are synthetic polymers, different from biological polymers, in particular different from polypeptides and proteins. They may, for example, be polycondensates of polyester or polyamide type, polyolefins, latices, (meth)acrylic polymers or vinyl polymers. The polymers are preferably polymers obtained from synthetic monomers. According to one preferred embodiment, the polymers are prepared by radical polymerization starting from at least one ethylenically unsaturated monomer, for example a mono-ethylenically unsaturated monomer, for example a mono-α-ethylenically unsaturated monomer. The radical polymerizations are generally carried out in the presence of a source of free radicals. They may especially be polymers prepared:

in solution in an aqueous reaction medium;
in solution in a reaction medium comprising a non-aqueous solvent, for example an alcohol, THF, toluene, a hydrocarbon, etc.;
in emulsion in a reaction medium comprising an aqueous external liquid and a non-aqueous internal polymerization phase (polymerization in direct emulsion phase, for example latex polymerization);
in emulsion in a reaction medium comprising a non-aqueous external liquid and an aqueous internal polymerization phase (polymerization in direct emulsion phase).

The polymerizations may use, other than solvents (aqueous or non-aqueous solvents) or dispersion liquids (aqueous or non-aqueous dispersion liquids), agents capable of initiating or catalyzing the polymerization, of controlling the kinetics thereof, of stopping the polymerization. Such agents are known and may be introduced into the reaction medium at an appropriate level of the downstream flow member, for example at the beginning of said member for a compound that initiates the polymerization, and at the end of said member for a compound that stops it.

The invention is particularly suitable for the preparation of polymers by polymerization in solution, especially an aqueous solution. It is possible, for example, to use polymerizations or copolymerizations of monomers chosen from the monomers of the following types (these types do not necessarily exclude one another):

water-soluble unsaturated neutral monomers;
anionic or potentially anionic unsaturated monomers; and/or
cationic or potentially cationic unsaturated monomers; and/or
zwitterionic unsaturated monomers; and/or
hydrophobic unsaturated monomers; and/or
amphiphilic unsaturated monomers.

As zwitterionic unsaturated monomers, mention may especially be made of:
sulfopropyldimethylammonium ethyl methacrylate (SPE)
sulfohydroxypropyldimethylammonium ethyl methacrylate (SHPE)
sulfopropyldimethylammonium propyl methacrylamide (SPP)
sulfopropyldimethylammonium ethyl methacrylate (SPDA)

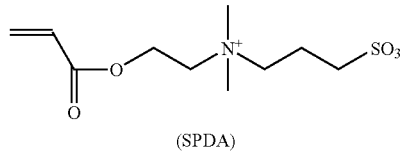

(SPDA)

sulfohydroxypropyldimethylammonium propyl methacrylamido (SHPP)
2-vinyl (3-sulfopropyl)pyridiniumbetaine (2SPV)
4-vinyl (3-sulfopropyl)pyridiniumbetaine (4SPV)
carboxybetaines.

As unsaturated hydrophilic neutral monomers, mention may be made of:
hydroxyalkyl esters of α,β-ethylenically unsaturated acids such as hydroxyethyl or hydroxypropyl acrylates and methacrylates, glycerol monomethacrylate, etc.;
α,β-ethylenically unsaturated amides, such as acrylamide (AM), methacrylamide, N-methylolacrylamide, dimethylacrylamide, dimethylmethacrylamide, etc.;
α,β-ethylenically unsaturated monomers bearing a water-soluble polyoxyalkylenated segment of the polyethylene oxide type, such as, where appropriate, the random or block polyethylene and/or polypropylene oxide α-methacrylates (BISOMER S20W, S10W, etc.; LAPORTE) or α,ω-dimethacrylates, etc.;
α,β-ethylenically unsaturated monomers that are precursors of hydrophilic units or segments such as vinyl acetate which, once polymerized, may be hydrolyzed to generate vinyl alcohol units or polyvinyl alcohol segments;
vinyl lactams such as vinylpyrrolidone;
α,β-ethylenically unsaturated monomers of ureido type and in particular 2-imidazolidinone ethyl methacrylamide optionally as a mixture (Sipomer WAM II from RHODIA);
and mixtures or combinations thereof.

As unsaturated potentially cationic monomers, mention may be made of:
N,N-(dialkylamino-ω-alkyl)amides of α,β-monoethylenically unsaturated carboxylic acids, for instance N,N-dimethylaminomethyl-acrylamide or -methacrylamide, 2-(N,N-dimethylamino)ethyl-acrylamide or -methacrylamide, 3-(N,N-dimethylamino)propyl-acryl-amide or -methacrylamide and 4-(N,N-dimethylamino)-butyl-acrylamide or -methacrylamide;
α,β-monoethylenically unsaturated amino esters, for instance 2-(dimethylamino)ethyl acrylate (ADAM), 2-(dimethylamino)ethyl methacrylate (DMAM), 3-(dimethylamino)propyl methacrylate, 2-(tert-butylamino)ethyl methacrylate, 2-(dipentylamino)ethyl methacrylate or 2-(diethylamino)ethyl methacrylate;
vinylpyridines;
vinylamine;
vinylimidazolines;
monomers that are precursors of amino functions such as N-vinylformamide, N-vinylacetamide, etc., which give rise to primary amine functions by simple acidic or basic hydrolysis.

As examples of unsaturated cationic monomers, mention may be made of:
ammoniumacryloyl or -acryloyloxy monomers, for instance:
trimethylammoniumpropyl methacrylate chloride;
trimethylammoniumethylacrylamide or -methacryl-amide chloride or bromide;
trimethylammoniumbutylacrylamide or -methacryl-amide methyl sulfate;
trimethylammoniumpropylmethacrylamide methyl sulfate (MES);
(3-methacrylamidopropyl)trimethylammonium chloride (MAPTAC);
(3-acrylamidopropyl)trimethylammonium chloride (APTAC);
methacryloyloxyethyltrimethylammonium chloride or methyl sulfate;
acryloyloxyethyltrimethylammonium chloride; or acryloyloxyethyltrimethylammonium methyl sulfate (ADAMQUAT Cl or ADAMQUAT MeS);
methyldiethylammonium ethyl acrylate methyl sulfate (ADAMQUAT MeS);
benzyldimethylammonium ethyl acrylate chloride or methyl sulfate (ADAMQUAT BZ 80);
1-ethyl-2-vinylpyridinium or 1-ethyl-4-vinylpyridinium bromide, chloride or methyl sulfate;
N,N-dialkyldiallylamine monomers such as N,N-diallyldimethylammonium chloride (DADMAC);
dimethylaminopropylmethacrylamide, N-(3-chloro-2-hydroxypropyl)trimethylammonium chloride (DIQUAT chloride);
dimethylaminopropylmethacrylamide, N-(3-methyl-sulfate-2-hydroxypropyl)trimethylammonium methyl sulfate (DIQUAT methyl sulfate);
the monomer of formula:

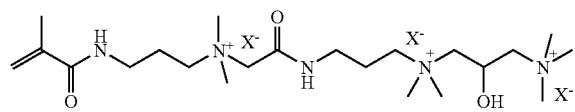

in which $X^-$ is an anion, preferably chloride or methyl sulfate.

As examples of unsaturated anionic or potentially anionic monomers, mention may be made of:
monomers containing at least one carboxylic function, for instance α,β-ethylenically unsaturated carboxylic acids or the corresponding anhydrides, such as acrylic, methacrylic or maleic acids or anhydrides, fumaric acid, itaconic acid, N-methacryloyl alanine and N-acryloylglycine and the water-soluble salts thereof;
monomers that are precursors of carboxylate functions, for instance tert-butyl acrylate, which generate, after polymerization, carboxylic functions by hydrolysis;
monomers containing at least one sulfate or sulfonate function or a corresponding acid function, for instance 2-sulfooxyethyl methacrylate, vinylbenzenesulfonic acid, allylsulfonic acid, 2-acrylamido-2-methylpropane-sulfonic acid, sulfoethyl acrylate or methacrylate, and sulfopropyl acrylate or methacrylate, and the water-soluble salts thereof;
monomers containing at least one phosphonate or phosphate function or a corresponding acid function, for instance vinylphosphonic acid, etc., ethylenically unsaturated phosphate esters such as the phosphates derived from hydroxyethyl methacrylate (Empicryl 6835 from Rhodia) and those derived from polyoxyalkylene methacrylates, and the water-soluble salts thereof.

As unsaturated amphiphilic monomers, mention may be made of:
polyethoxylated and/or polypropoxylated $C_3$-$C_{30}$ aliphatic alcohol acrylates or methacrylates, the aliphatic part of which is, where appropriate, substituted by one or more hydroxyl(s), preferably at the end of the aliphatic group, for example SIPOMER BEM from Rhodia (ω-behenyl polyoxyethylene methacrylate optionally as a mixture), SIPOMER HPM100 from Rhodia, PLEX6877-0;
polyethoxylated and/or polypropoxylated polystyrylphenol acrylates or methacrylates, for example SIPOMER SEM-25 from Rhodia (ω-tristyrylphenyl polyoxyethylene methacrylate);
polyethoxylated and/or polypropoxylated alkylphenol acrylates or methacrylates.

As unsaturated hydrophobic monomers, mention may be made of:
vinylaromatic monomers such as styrene, alpha-methylstyrene, para-chloromethylstyrene, vinyltoluene, etc.;
vinyl or vinylidene halides, for instance vinyl chloride or vinylidene chloride;
$C_1$-$C_{30}$, preferably $C_4$-$C_{22}$ alkyl esters of α,β-monoethylenically unsaturated acids such as methyl, ethyl, butyl, 2-ethylhexyl, isoactyl, lauryl, isodecyl or stearyl acrylates or methacrylates;
vinyl or allyl alcohol esters of saturated carboxylic acids such as vinyl or allyl acetates, propionates, versatates, stearates, etc.;
α,β-monoethylenically unsaturated nitriles containing from 3 to 12 carbon atoms, for instance acrylonitrile, methacrylonitrile, etc.;
α-olefins, for instance ethylene, propylene, etc.;
conjugated dienes, for instance butadiene, isoprene, chloroprene; and
mixtures or combinations thereof.

Any source of free radicals may be used. It is possible, in particular, to generate free radicals spontaneously, for example by raising the temperature, with suitable monomers such as styrene. It is possible to generate free radicals by irradiation, especially by UV irradiation, preferably in the presence of appropriate UV-sensitive initiators. It is possible to use initiators (or "triggers") or systems of initiators, of radical or redox type. The source of free radicals may or may not be water-soluble. Use will preferably be made of initiators that are water-soluble, or at least partially water-soluble (for example water-soluble to at least 50% by weight).

Use may in particular be made of the following initiators:
hydrogen peroxides such as: tert-butyl hydroperoxide, cumene hydroperoxide, t-butyl peroxyacetate, t-butyl peroxybenzoate, t-butyl peroxyoctoate, t-butyl peroxyneodecanoate, t-butyl peroxyisobutarate, lauroyl peroxide, t-amyl peroxy-pivalate, t-butyl peroxypivalate, dicumyl peroxide, benzoyl peroxide, potassium persulfate, ammonium persulfate;
azo compounds such as: 2,2'-azobis(isobutyronitrile), 2,2'-azobis(2-butanenitrile), 4,4'-azobis(4-pentanoic acid), 1,1'-azobis(cyclohexane-carbonitrile), 2-(t-butylazo)-2-cyanopropane, 2,2'-azobis[2-methyl-N-(1,1)-bis(hydroxymethyl)-2-hydroxy-ethyl]propionamide, 2,2'-azobis(2-methyl-N-hydroxy-ethyl]propionamide, 2,2'-azobis(N,N'-dimethylene-isobutyramidine) dichloride, 2,2'-azobis(2-amidinopropane) dichloride, 2,2'-azobis (N,N'-dimethyleneisobutyramide), 2,2'-azobis(2-methyl-N-[1,1-bis(hydroxymethyl)-2-hydroxyethyl]propionamide), 2,2'-azobis(2-methyl-N-[1,1-bis (hydroxymethyl)ethyl]-propionamide), 2,2'-azobis[2-methyl-N-(2-hydroxyethyl)-propionamide], 2,2'-azobis (isobutyramide) dihydrate;

redox systems comprising combinations such as:
  mixtures of hydrogen or alkyl peroxides, peresters, percarbonates and similar compounds and any iron salts or titanium salts, zinc formaldehyde sulfoxylate or sodium formaldehyde sulfoxylate, and reducing sugars;
  persulfates, perborate or perchlorate of alkali metals or of ammonium in combination with an alkali metal bisulfite, such as sodium metabisulfite, and reducing sugars; and
  alkali metal persulfates in combination with an arylphosphinic acid such as benzenephosphonic acid and other similar compounds, and reducing sugars.

THE BRIEF DESCRIPTIONS OF THE DRAWINGS

The invention will be described below, with reference to the appended drawings, given solely by way of non-limiting examples, in which:

FIG. 4 is a front view, similar to FIG. 1, illustrating an additional embodiment variant of the invention;

FIGS. 5A and 5B are respectively schematic and front views, illustrating means for maintaining at a given temperature, that equip the installation from the preceding figures;

Figure 1:
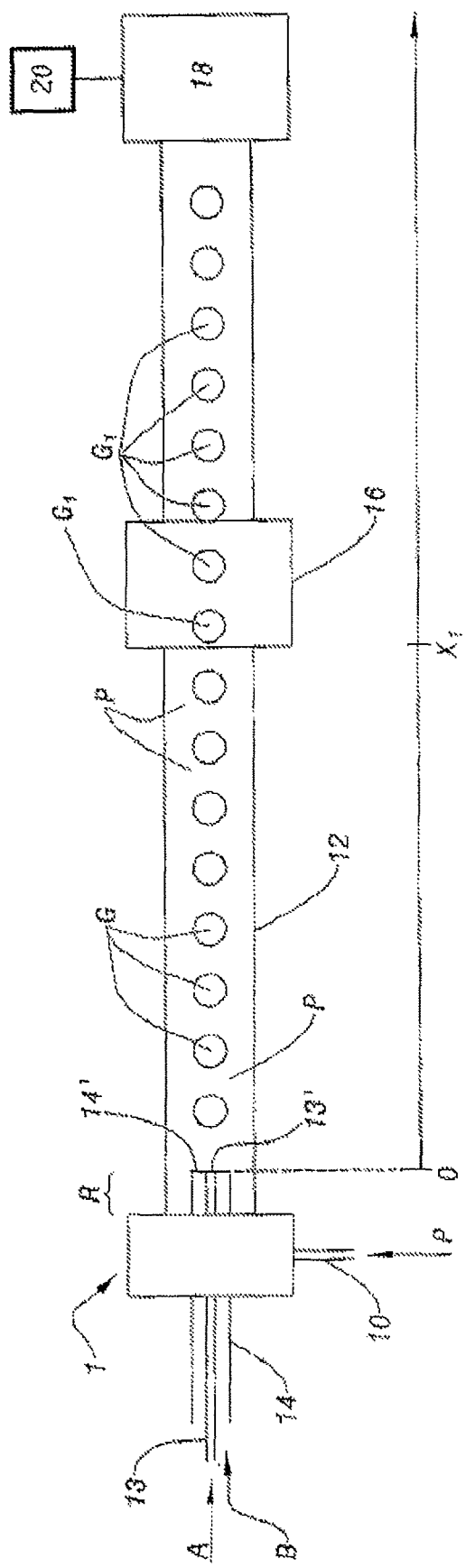
FIG. 1 is a front view illustrating an installation for polymer preparation in accordance with the invention.

It is noted that, according to one embodiment, an analysis may be carried out at a point of the tubular flow member known as the downstream tubular flow member, for example by techniques of spectroscopic type (UV spectroscopy, infrared spectroscopy, light-scattering spectroscopy, X-ray scattering spectroscopy, Raman spectroscopy, fluorescence spectroscopy, etc.) or of optical type (microscopy, image analysis, etc.) which may for example give information on the progress of a reaction (by metering of the products formed or of the residual reactants, for example in the case of a polymer, by metering residual amounts of monomers). The suitable analysis means are, for this method, located in the vicinity of the tubular flow member, at one or more given point(s) along the member. It is not excluded to move the analysis means in order to obtain information by measurements at various points of the flow and therefore at various stages of progress of the conversion. It is not excluded either to place several analysis means, which are identical or different, along the tube. It is not excluded either that a single analysis means may give information on several points of the tube, for example an optical analysis via photography optionally with image processing. According to another embodiment, which does not exclude the first embodiment (it may be combined), the analysis may be carried out directly at the outlet of the tubular flow member, for example without recovering/isolating the reaction medium, where appropriate constituted of the plugs exiting said member, for example by chromatography techniques, especially size exclusion chromatography adapted to the analysis of polymers, which may for example give information on the exact composition of the polymer, such as its average molecular weight, the distribution of the macromolecular chains, the polydispersity index.

It is noted that, according to one embodiment, the reaction medium is recovered, where appropriate constituted of the succession of plugs, and the polymer is optionally isolated. The reaction medium or the isolated polymer is then used: it may for example be sold or sampled and be the subject of an application, for example it may be put into a formulation with other compounds.

It is noted that, according to one embodiment, it is possible to test the polymer, for example with respect to a usefulness in an application. The test may especially comprise a phase of putting it into a formulation with other compounds, and a phase of evaluating the formulation obtained.

The invention may thus be most particularly appropriate for uses or tests of uses in the following applications:
  cosmetic formulations;
  detergent formulations;
  formulations for household care products, especially for cleaning dishes in a machine or by hand, for cleaning laundry in a machine or by hand, for cleaning hard surfaces (for example floors, furniture, and kitchen or bathroom surfaces);
  surface treatment formulations;
  formulations for coatings, especially paints;
  pigment formulations, especially ink formulations;
  fluid formulations used in oil and/or gas exploitation;
  water treatment; and/or
  plastic formulations.

Figure 2A:
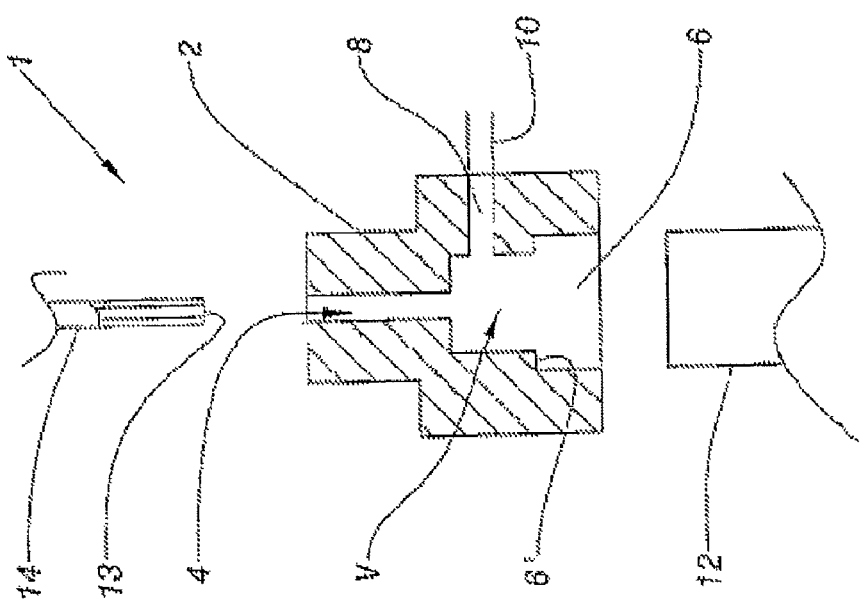
FIGS. 2A and 2B are front views illustrating a module for generating plugs that belongs to the installation from FIG. 1, in which the various components are respectively dismantled and assembled with respect to one another.
Figure 2B:
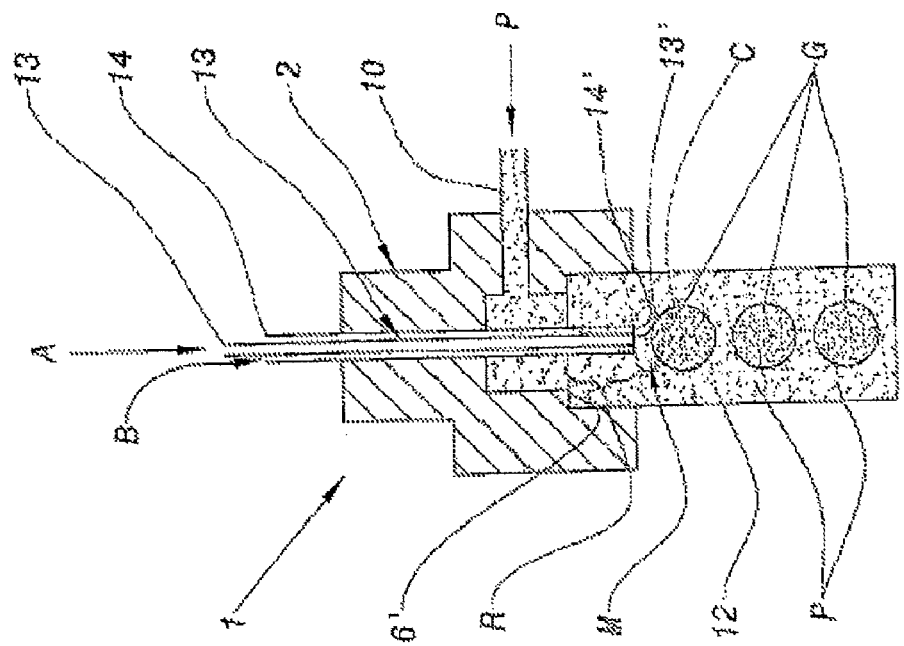

The installation according to the invention of FIG. 1 firstly comprises a module for generating plugs, represented schematically on this figure but that is illustrated more precisely in FIGS. 2A and 2B. This module, denoted in its entirety by the reference 1, firstly comprises a coupling member 2 that is more or less cylindrical, made from any appropriate material, especially a metallic or else plastic material. This coupling member 2 has an internal volume V, that communicates with the outside via three different paths.

For this purpose, this member 2 is firstly provided with an upper channel 4 and a lower chamber 6, with reference to FIGS. 2A and 2B. This channel 4 and this chamber 6, which are co-axial, have a cross section respectively below and above that of the internal volume V. Furthermore, the coupling member 2 is bored by a channel 8, known as a side channel, provided on the right in FIGS. 2A and 2B. A nozzle 10, made for example from PEEK, PTFE, silicone or else of metal, is attached by any suitable means to the walls of the opening of this side channel 8.

The coupling member 2 is joined to various tubular flow members, which will be described in what follows. In the meaning of the invention, a tubular flow member is an elongated flow member of closed section, the transverse profile of which may have any type of shape, in particular oval or square. In the meaning of the invention, such a member is not made in a solid body, such as for example a microchannel that is etched into a wafer.

This member is thus bordered by a thin peripheral wall. Unlike microfluidic embodiments, that require two wafer parts to be put together, especially by bonding, this tubular flow member is capable of being made from a single piece, advantageously.

The various tubular flow members to which the invention refers may be made from a rigid material, such as for example steel. However, alternatively, it is possible to make provision for producing them from a semi-rigid, or even flexible material such as for example PTFE, a silicone, PVC, polyethylene or PEEK.

As a variant, it is also possible to make use of a fluorinated product, especially of PFA type. The flow members may also be made from a molten silica, covered with polyimide, which it is possible to remove locally in a known manner, especially by means of sulfuric acid, in order to visualize the inside of the flow member.

Initially, a first tubular flow member is provided, namely a capillary 12 made, for example, from PTFE or silicone, which has an equivalent internal diameter typically between 10 micrometers and 50 mm. In addition, there are two other tubular flow members, namely two other capillaries 13 and 14 made, for example, of PEEK.

The capillary 13 has an equivalent diameter less than that of the capillary 14 given that, as will be explained in detail in what follows, this capillary 13 penetrates in operation into the internal volume of the capillary 14. In this respect, the typical values of the equivalent diameters are respectively 50 micrometers for the inner capillary 13 and 250 micrometers for the outer capillary 14. Furthermore, this outer capillary 14 has an equivalent diameter that is less than that of the capillary 12. Finally, given that the capillary 13 penetrates into the capillary 14, its outer diameter is less than the internal diameter of the peripheral capillary 14.

In the present text, the expression "equivalent diameter" of the various flow members is understood to mean the diameter that the inner walls of these members would have, for a same surface area, if they were of circular cross section. In the case where they are circular, this equivalent diameter obviously corresponds to the internal diameter of these members.

In order to constitute the module 1 itself, it is firstly a question of pushing the outer capillary 14 into the channel 4, while positioning the inner capillary 13 inside the volume of this outer capillary 14. The capillary 12 is also placed in the chamber 6, until its end comes to rest against the shoulder 6' separating this chamber 6 from the internal volume V.

The outer capillary 14, which is centered and guided inside the channel 4, is pushed until it juts out beyond the shoulder 6'. In other words, the opposite walls of the capillaries 12 and 14 form an overlap zone, denoted by R, which extends immediately downstream, namely below the shoulder 6' in FIG. 2B. Furthermore, the downstream end 13' of the inner capillary 13 is flush with the downstream end 14' of the outer capillary 14. In other words, these two downstream ends occupy the same axial position, with reference to the main axes of the various capillaries 12, 13 and 14.

Furthermore, the upstream capillaries 13 and 14 receive means for injecting two fluids, of the type known per se. The means for injecting each fluid comprise a tube that is not represented of flexible type, which is associated with a syringe and a syringe pump, which are also not represented. Similarly, the nozzle 10 cooperates with the means for injecting a third fluid, which comprise for example a supplementary tube, that is also flexible, which is associated with a syringe and a syringe pump that are not represented.

Again with reference to FIG. 1, the downstream capillary 12 leads into a tank 16, provided with conventional refrigeration means. This tank is consequently suitable for carrying out a quench of the polymerization that takes place in the capillary 12, as will be seen in what follows. Finally, downstream of the quench tank 16, the capillary 12 is brought into communication with an analysis unit 18 (optional) of chromatograph type, itself connected to a computer processor 20 (optional).

An implementation of a process comprising a preparation of a polymer, carried out using the installation described above, will now be explained in what follows.

It is a question of injecting, into the two downstream capillaries 13 and 14, two fluids A and B suitable for forming a mixture, which is itself capable of undergoing a polymerization. As a purely non-limiting example, these two fluids may generate a radical polymerization reaction, for example starting from (co)monomers, especially water-soluble (co)monomers, such as acrylic acid and/or diallyldimethylammonium chloride (DADMAC). More information regarding the monomers, polymers and mixtures which may be suited to the implementation thereof are given above.

Furthermore, an auxiliary fluid P, which is not miscible with the mixture of the aforementioned two first fluids, is injected via the nozzle 10. The typical injection flow rate of these various fluids is, for example, between 500 μl/h and 50 ml/h. The ratio of, on the one hand, the flow rate of auxiliary fluid P to, on the other hand, the sum of the flow rates of the two fluids A and B is for example between 0.5 and 10. Advantageously the flow rate of auxiliary fluid P is greater than the sum of those of A and B, for example with a ratio close to 2.

The auxiliary fluid then flows into the internal volume V, more precisely into the annular space formed by the opposite walls of the two capillaries 12 and 14. Moreover, immediately downstream of the downstream ends 13' and 14' of the upstream capillaries 13 and 14, the two first fluids are brought into mutual contact, in a zone known as the mixing zone, denoted by M. Thus, the two reactant fluids, which flow in the respective capillaries 13 and 14, are found only at this mixing zone, and not before the latter.

Furthermore, immediately downstream of the overlap zone R, these two fluids A and B are brought into contact, in a zone known as a contact zone denoted by C, with the immiscible carrier fluid P. The presence of this zone R makes it possible to visualize the formation of the drops, also known as "plugs", which allows the user to control the procedure. This is because, in the absence of such an overlap zone, the drops would be formed within the coupling member 2, which is not necessarily transparent.

Given that the carrier fluid P is not miscible with the fluids A and B, drops (or "plugs") G, each of which is constituted by the mixture of A and of B, are formed in the contacting zone C. It will be noted that these drops G form plugs, that themselves form a reaction medium in the meaning of the invention. It should be noted that in the present invention, the plugs preferably occupy, in a section of the fluid member, at least 10% of the surface area of said section, preferably at least 25%, preferably at least 50%, preferably at least 75%, preferably at least 90%, for example 100%. Therefore, the plugs have sizes of the same order as that of the carrier size, and may be distinguished from an emulsion of droplets in the carrier phase. Therefore, the assembly of the carrier phase and of the succession of plugs may be different from an emulsion polymerization system, especially from a conventional system of latex or inverse emulsion type polymerization. Preferably, an emulsifier (surfactant or other) is not used in order to obtain the plugs.

By independently setting the respective flow rate, on the one hand, of the two fluids A and B and, on the other hand, of the carrier fluid P, it is possible to form, immediately downstream of the capillaries 13 and 14, monodisperse drops G of dispersed phases. Given that these drops are emitted at a constant frequency denoted by f, their volume v is given by the formula v=q/f, where q is equal to the sum of the flow rates of A and B. In other words, the measurement of the frequency f, for example using a simple laser pointer that illuminates a photodiode, makes it possible to acquire the volume v of the drops G without having recourse to more taxing image processing techniques. Thus, for a given geometry, namely of the fixed diameters of capillaries 12, 13 and 14, it is possible to vary the size of the drops formed in a simple manner by only modifying the flow rate of the various immiscible fluids.

The various drops G thus produced then flow into the downstream capillary 12, that is the site of the formation of the polymer (polymerization). Thus, during the progression of the drops G in this capillary, the polymerization occurs, namely the nature of the mixture formed by the initial fluids A and B is gradually modified, depending on the state of progress of the polymerization. In other words, the most recently formed drop, namely that located on the far left-hand side in FIG. 1, comprises the two components A and B, which are not significantly mixed. Then, on moving downstream, these two components are increasingly better mixed in the following drops. Then, still further downstream, the polymerization that it is desired to study or use is increasingly advanced.

In this respect, it is advantageous that the characteristic time of this conversion is substantially greater than the mixing time of the two components. This makes it possible to emphasize that the process according to the invention most particularly finds its application in the study of slow conversions, such as slow chemical reactions.

As in the case of the microfluidic techniques mentioned in the preamble of the present description, the drops G thus form reactors of reduced size that flow at a constant rate, so that there is also an equivalence between the distance that they have traveled and the reaction time. In FIG. 1, the axis XX is noted, the origin O of which corresponds to the zone M, namely the formation of the drops G. Thus, a drop G located at a given point of the capillary 12, namely a given abscissa of this reference point, is representative of the polymerization at a given instant.

It will also be noted that it is advantageous to mix the two initial fluids A and B, in a mixing zone M that is substantially merged with the contacting zone C to bring into contact with the carrier fluid P. Specifically, no contact consequently occurs between the two initial fluids A and B before the formation of the drops G, so that the origin O associated with the polymerization corresponds to the instant when these two fluids A and B are admitted into the downstream capillary 12. In other words, with reference to FIG. 1, the origin O of the X-X axis of the distances, mentioned above, is identified in a particularly clear manner.

This therefore gives a great accuracy to the study of the polymerization, carried out in accordance with the invention. Furthermore, in the case where a polymerization is studied that results in the formation of a solid or very viscous product, this measurement makes it possible to prevent any blocking phenomenon. Specifically, if the two reactants were brought into contact before the formation of the drops, the aforementioned solid or very viscous product would be capable of obstructing the corresponding flow member.

Then, when the drops G are admitted into the capillary zone 12 that extends into the refrigerated tank 16, the polymerization undergone by these drops is stopped, under the effect of the quench induced by the low temperature in the tank 16. Under these conditions, all the drops $G_1$ that flow downstream of this tank 16 are of the same nature and correspond to a reaction time $t_1$, itself associated with the abscissa $X_1$ (see FIG. 1) corresponding to the opening of the capillary 12 into the tank 16.

Under these conditions, downstream of the tank 16, a settling phenomenon occurs due to the difference in density between the drops and the carrier phase. These thus separated drops then lend themselves in a convenient manner to an analysis, by means of the chromatograph 18. The computer 20 then processes the data supplied by the chromatograph 18, so as to determine at least one desired parameter of the aforementioned conversion.

Furthermore, if the flow rate of the components A and B is modified, the time $t_1$, associated with the abscissa $X_1$ of the tank 16, which corresponds to the time elapsed since the formation of the drops, will also be modified. In this way it is possible to analyze the conversion at various stages, without however moving the quench tank 16. Thus, for a given length of the capillary 12, for example 1 meter, it is possible to vary the residence time between 5 minutes and 1 hour, by means of a simple modification of these flow rates.

Figure 8:
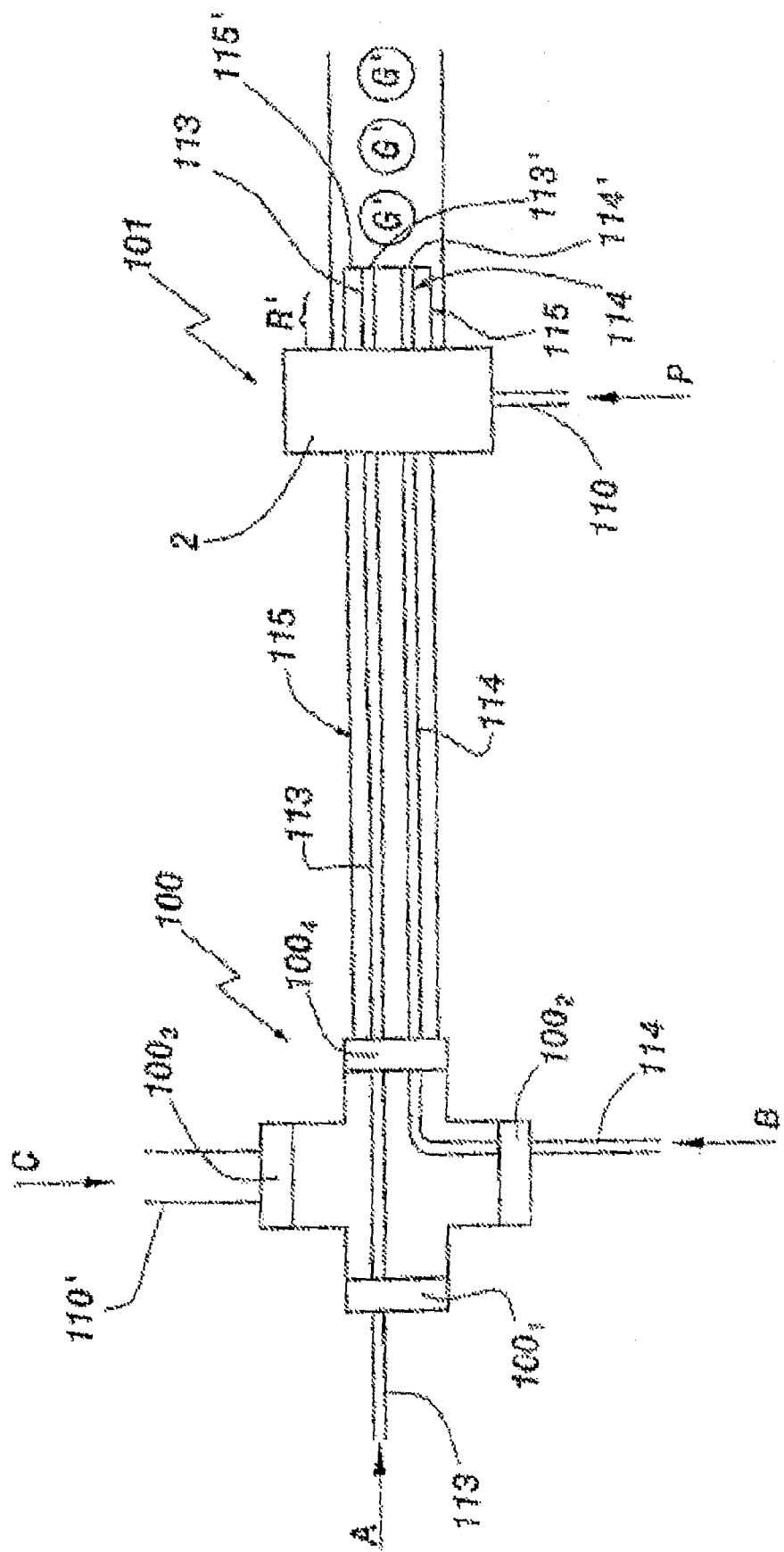

One embodiment variant of the invention is illustrated in FIG. 8. In the latter, the mechanical components similar to those from FIG. 1 are allocated therein the same reference numbers, increased by 100.

Firstly there is an upstream member 100, which is intended to assemble several capillaries, without however providing a role of mixing of the fluids circulating in these capillaries. This member 100, which is hollow, overall defines a cross shape that has three inlets $100_1$, $100_2$ and $100_3$, and also an outlet $100_4$. Two capillaries 113 and 114 penetrate into the hollow body, through the first two inlets $100_1$ and $100_2$.

However, contrary to the first embodiment, these two capillaries 113 and 114 are not concentric, but are placed side by side, so as to extend through the outlet $100_4$. It will be noted that the capillary 114 is bent in the hollow body of the member 100. Furthermore, the third inlet $100_3$ is put into communication with a nozzle 110', the role of which will be explained below.

Finally, the outlet $100_4$ of the upstream member 100 leads into a third capillary 115, having a larger dimension than those capillaries 113 and 114. Thus, downstream of this outlet $100_4$, the capillaries 113 and 114 are arranged side by side, while being surrounded by the peripheral wall of the capillary 115.

These three capillaries 113 to 115 then lead into a module 101, similar to that labeled 1 from FIG. 1. The module 101 comprises, in particular, a coupling member 102, and also a nozzle 110.

Downstream of the module 101, there is a capillary 112, similar to the capillary 12, which has a diameter greater than that of the peripheral capillary 115. In a similar manner to the first embodiment, the downstream ends 113', 114' and 115' of the three capillaries 113 to 115 are flush with one another, namely they occupy the same axial position. Furthermore, the opposite walls of the capillaries 112 and 115 form an overlap zone denoted by R'.

The formation of drops, in the capillary 112, takes place in the following manner. Two fluids A and B capable of forming a mixture are injected into the capillaries 113 and 114. Furthermore, a fluid C is injected from the nozzle 110' toward the capillary 115, via the hollow body of the member 100.

This fluid C may be a third reactant, capable of reacting with the fluids A and B. As a variant, C may be a fluid comprising an adjuvant, such as a catalyst or an initiator or a solvent, which may or may not intervene in the actual nature of the reaction, and which may involve its parameters, such as its speed.

Finally, as in the embodiment from FIG. 1, an auxiliary fluid P, which is not miscible with the three first fluids A, B and C, is injected via 110. Under these conditions, immediately downstream of the overlap zone R', drops G' are formed in a similar manner to what was described with reference to FIG. 1.

As a variant, it is possible to place at least one other capillary, such as capillary 113 or 114, inside the peripheral capillary 115. Each other capillary allows the flow of a supplementary fluid, which may be a reactant or may be an adjuvant for the reaction.

The embodiment from FIG. 8 has specific advantages, in terms of size. Thus, it is possible to make use of at least two capillaries having a small section, such as capillaries 113 and 114, which are placed side by side inside a single capillary 115 of larger section.

Figure 3:
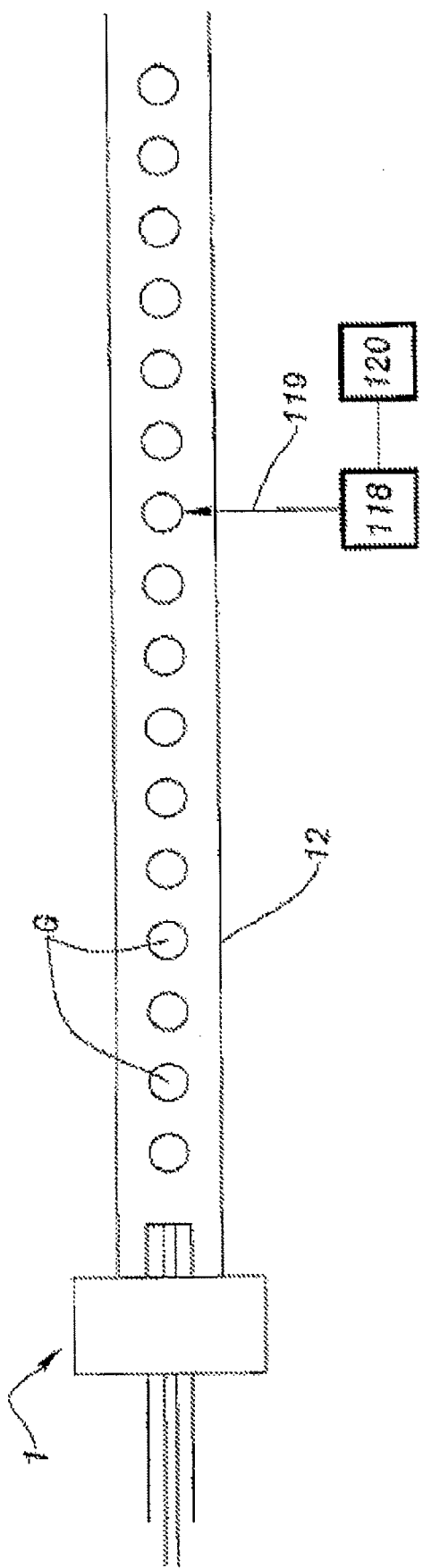
FIG. 3 is a front view, similar to FIG. 1, illustrating an embodiment variant of the invention.

FIG. 3 illustrates an embodiment variant of the invention, which does not use a quench tank 16, or a chromatograph 18. In this variant, an analysis is consequently not carried out off-line as in the embodiment from FIG. 1, but on-line using a beam type analyzer. This is in this case a Raman unit 118, the beam 119 of which is pointed toward the downstream capillary 12, which is associated with a computer 120.

Thus, in FIG. 3, an analysis is carried out in a zone where the polymerization takes place whereas, in the first embodiment from FIG. 1, an analysis is carried out after the stoppage of this polymerization. The beam 119 is pointed toward a same spot of the capillary 12, and an analysis of several successive plugs, flowing past at this spot, is carried out. This makes it possible to acquire a significant number of pieces of information regarding the progress of the polymerization at this given spot.

Alternatively, the beam 119 may be displaced axially, so as to acquire abscissas of the capillary 12 and, consequently, at different polymerization times. As in the first embodiment, it is also possible to modify the flow rate of the components A and B that form the drops G, so as to modify the polymerization time for which the analysis is carried out, without however modifying the position of the beam 119.

At the end of the implementation of the steps described above, it was possible to determine at least one parameter of a physical and/or chemical conversion of the polymer and/or of the polymerization. It is then possible to restart this series of steps with another conversion, involving another reaction medium and/or other operating conditions. These steps are carried out iteratively for an entire range of polymers and/or polymerizations so that, at the end of the screening process thus implemented, it is then possible to identify therefrom at least one product of interest depending on the targeted application.

FIG. 4 illustrates an additional embodiment variant of the invention. In the latter is the capillary 12 in which some first plugs $G_0$ have been formed in a similar manner to what was described above. Then, at least one other component that it is desired to introduce into each primary drop $G_0$ is injected using a needle 30 that has pierced this capillary 12. This leads to the formation of definitive drops G, which may then be treated in the manner conforming to the embodiment described previously. Several such injections may be carried out. It is thus possible to modify and/or rectify the composition of the reaction medium along the flow member. It is especially possible to inject monomers and/or initiators again. According to one particular embodiment, a control type polymerization is used, for example a controlled radical polymerization, that carries out a first phase of polymerization starting from a monomer or a mixture of monomers, before injection, then a second phase of polymerization starting from a different monomer or a mixture of monomers, to obtain block copolymers.

Thus, each primary drop $G_0$ may be formed from a first monomer, and also from a polymerization initiator. Then, via the needle 30, it is possible to inject a second monomer, which makes it possible to form copolymer blocks. It is also possible to add again, via this needle 30, a supplementary amount of initiator, especially in the case where the latter is no longer active, and/or a supplementary amount of (co)monomers, and thus to ensure a homogeneous (co)polymerization.

It will also be noted that it is possible to pierce several needles, such as the needle 30, at different successive sites of the main capillary 12. It will finally be noted that the or each needle 30 may be replaced by a pipe, of reduced transverse dimension.

The needle 30, combined with the capillary 12, may enable the implementation of an embodiment variant of the invention. In this variant, not represented as such, drops are withdrawn from the capillary 12. For this purpose, this needle 30 has a sufficient diameter in order not to damage these drops.

This needle 30 also contains a product capable of stopping the reaction that takes place within the drops. Under these conditions, it is possible to adjust the residence time of the drops, at the moment of this withdrawal, by varying the corresponding flow rates. It is then possible to carry out various withdrawals, which correspond to different stages of the reaction taking place in the drops.

FIGS. 5A and 5B illustrate a particularly useful embodiment variant of the invention, in which the capillary 12 is made from a flexible material, while being combined with a heating body 50, that makes it possible to maintain this flexible tube 12 at a given temperature. This heating body 50, which has a cylindrical shape, defines an internal volume V that is open at its two axial ends (see FIG. 5A, where this heating body is represented schematically).

This internal volume is bordered by a wall 52, etched into the outer periphery of which are grooves 55 for receiving this tube. These grooves extend, for example, in a helical manner. It will also be noted that it is possible to etch different grooves, suitable for receiving tubes of different diameters.

An outer flange 54 (see FIG. 5B), for example made of aluminum, covers the wall 52, which makes it possible to confine the tube 50 in order to optimize the thermal control. Furthermore, the presence of this flange 54 makes it possible to keep the flexible tube 12 in position, in contact with the cylindrical wall 52.

The open ends of the body 50 are connected to a cryostat 56 (see FIG. 5B) of a type that is known per se, which ensures the closed-circuit circulation of a heat transfer fluid. The latter then ensures that the flexible tube 12 is kept at a given temperature, so that the conversion that it is desired to study takes place under predetermined temperature conditions. Finally, the outer flange 54 defines a median window 58, that makes it possible to visualize the flexible tube 12. Under these conditions, it is possible to carry out characterizations of an optical nature of the conversion, by on-line analysis.

The embodiment from these FIGS. 5A and 5B therefore makes it possible to carry out conversions while maintaining them at the desired temperature, which is capable of varying, for example, from −20 to 200° C. The on-line analysis which may be carried out is, for example, of Raman spectroscopy or else infrared thermography type. Furthermore, it is possible to arrange a large length of flexible tube 12 around the cylindrical wall 52. Under these conditions, the residence time that it is possible to achieve, in the part of this flexible tube wound around this cylinder can attain several hours.

The embodiment associated with FIGS. 5A and 5B is particularly practical and advantageous. It makes it possible, in particular, to prepare polymers and to study reactions in wider fields than those which were hitherto accessible. Moreover the implementation of the invention makes it possible to:

operate under conditions of a high solids content (concentration of the monomers and/or of the polymer) in the reaction medium, which is more effective in process terms and may make it possible to avoid subsequent concentration operations; and/or implement a good control of the temperature, by providing heat for endothermic reactions, and most often by discharging heat for exothermic reactions; and/or being able to handle reaction products of high viscosity.

Figure 6:
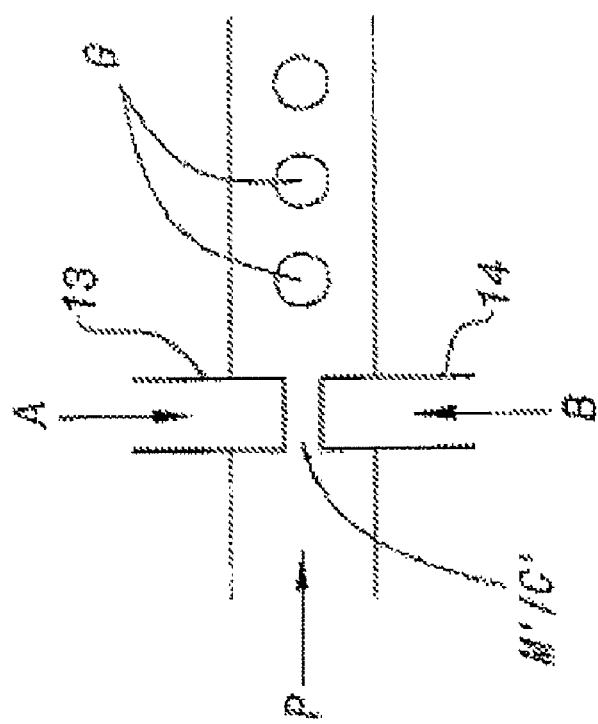

FIG. 6 illustrates a supplementary embodiment variant of the invention, in which the capillaries 13 and 14 open laterally into the capillary 12. Under these conditions the mixing zone M', which is merged with the contacting zone C', is located between the opposite ends of these two capillaries.

Figure 7:
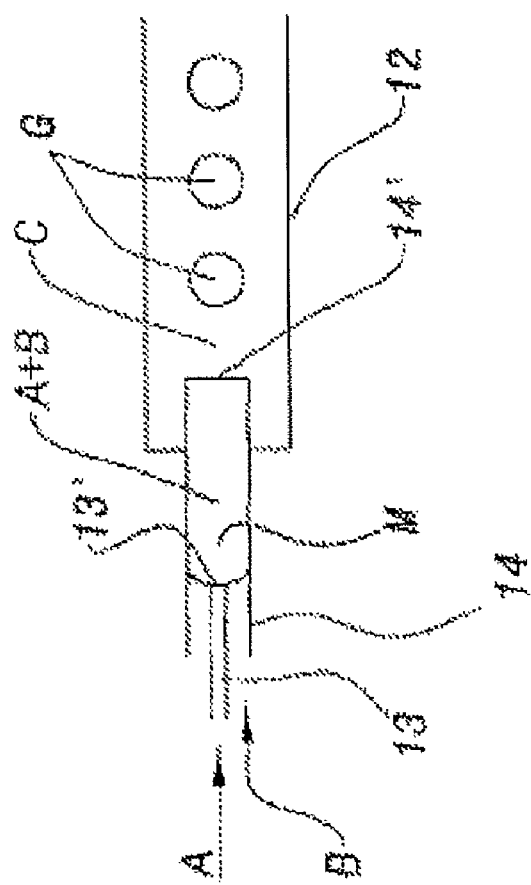
FIGS. 6 to 8 are front views, similar to FIG. 1, illustrating two additional embodiment variants of the invention.

FIG. 7 illustrates a supplementary embodiment variant of the invention, in which the capillary 13 is not flush with the downstream end of the outer capillary 14. In other words, the end 13' is located upstream of the end 14', whilst a mixture M formed from A and from B flows in the vicinity of the latter end. In this way, the reactants intended to form the drop are brought into contact before the actual formation of this drop. This embodiment lends itself to the flow of reactants, the mixing of which is not of the type to form a solid capable of blocking the capillary 13.

Referring again to FIG. 8, it will be noted that, as a variant, the capillary 113 and/or the capillary 114 may not be flush with the downstream end 115' of the outer capillary 115. Under these conditions a mixture is formed between the fluid C and also the fluid A and/or the fluid B, before the formation of the drops G'. In other words, the mixing zone is then located upstream of the end of the capillary 115.

It will also be noted that it is possible to form drops G from more than two components, in a manner different to that described in FIG. 8. Thus, it is possible to use several concentric capillaries, each of which ensures the flow of one of these components. It is also possible to use only two concentric capillaries, as in the example from FIG. 1, while making at least two reactants flow in at least one of these tubes.

It will be noted that the length of the capillary 12 may advantageously be between 50 cm and 10 meters, preferably between 1 and 4 meters. Under these conditions, the residence time of each drop is, for example, between 2 minutes and 10 hours.

It is noted that it is possible to stop the injection of reactants, through the capillaries 13 and 14, at a given moment. Under these conditions, the drops present in the capillary 12 are then immobilized, while the polymerization continues to take place. Then, at the end of this immobilization time, which allows the conversion to progress, reactants are again injected via the upstream capillaries 13 and 14, which makes it possible to make the drops flow again in the capillary 12.

At least some of the various operations described above may be controlled by computational means, of computer type. Under these conditions, the latter is capable, in particular, of automatically generating the successive compositions of the reaction medium, where appropriate plugs, that flow in the capillary 12, of controlling the temperature of the heating body 50, of acquiring the analysis data and of automating a sample collection.

The invention may especially be used in order to prepare samples of products to be tested, or even in order to prepare products on an industrial scale, especially by radical polymerization.

The invention makes it possible to achieve the aforementioned objectives.

The merit of the Applicant having brought to light certain drawbacks linked to the microfluidic technique presented in the preamble of the present description will first be underlined.

Specifically, microfluidic devices require, in view of their fabrication, the use of expensive soft lithography techniques, which require a substantial financial investment and a significant expertise in the field. This is why these techniques are not currently available in the majority of industrial laboratories.

Furthermore, a microfluidic type chip is not adjustable given that, in order to modify part of its hydraulic circuit, it is necessary to fabricate it again.

Furthermore, the very small dimensions of microfluidic devices requires a corresponding miniaturization of the analysis tools. This is not always easy to implement, while being accompanied by significant cost premiums.

The residence times of a plug on a microfluidic chip of conventional size are relatively short. It is consequently impossible to study the kinetics of slow chemical reactions, the characteristic time of which is a few minutes to several hours.

Finally, the displacement, stoppage and needling of plugs in an array require the use of mechanical members of valve type. On a microfluidic scale, such a use proves particularly tricky to implement.

However, the present invention makes it possible to overcome these various drawbacks.

Specifically, the invention makes good use of a flow that takes place on a larger scale, of "millifluidic" type, which makes it possible to obtain substantially larger plug volumes and flow rates. Furthermore, the flow members used in the invention are not made in a solid body, of wafer type, which is advantageous in terms of costs.

The use of a scale much higher than microfluidics, associated with the use of adjustable flow members, makes it possible to increase the residence time of the reaction medium, where appropriate of the plugs.

Furthermore, it will be noted that the millifluidic flow according to the invention makes it possible to produce articles, such as complex plugs, which cannot be obtained simply by means of microfluidic flows. Under these conditions, the invention makes it possible, in particular, to generate double emulsions which it is not possible to create in a simple manner in microfluidics.

It should also be noted that the fluid flow rates used in the invention are typically between 1 and 1000 ml/h, i.e. between a few tens of milliliters and a few tens of liters per day. By comparison, the flow rates permitted by microfluidics are substantially lower, namely below a few tens of milliliters per day.

The invention may especially find very advantageous applications, by virtue of the information provided, in the design of processes for preparing polymers, in the design of novel polymers, or polymerization processes. The invention also offers a great simplicity of use, and numerous possibilities for variations in the number and the order of the reactants used: it is thus possible to introduce certain reactants after others (for example catalysts or initiators or comonomers or a reactant used in a second synthesis step), where appropriate by trying several introduction points (or moments), without having to significantly modify a microfluidic reactor design or item of equipment.

Finally, it will be noted that the invention makes it possible to retain the advantages specific to microfluidics, in the sense that it allows substantially the same plug management operations.

The process of the invention may also make it possible to achieve high average molecular weights and/or to operate with high solids contents, for example with solids contents greater than 40% by weight of the reaction medium, or even greater than 50%. Such solid extracts of reaction mediums cannot be used in conventional polymerization processes, especially those that use jacketed batch reactors, in particular during radical polymerizations in aqueous solution, since the viscosity then becomes very high, and/or since they do not allow a sufficient discharge of heat. High molecular weights are also difficult to achieve without an effective discharge of heat (too high a heat may initiate the polymerization of too many chains and therefore limit the accessible sizes of each) and/or without a good manipulability at high viscosity that may enable a reaction medium in the form of a succession of plugs.

The process may especially make it possible, from a product point of view, to widen the range of operating conditions (temperature, monomer concentration, etc.), to make it possible to attain different polymer structures, to better control the molecular weight, and/or to improve the usage properties, and from an industrial point of view to facilitate the extrapolation, and/or to improve the robustness of the process.

Certain advantages of the invention will appear in view of the following non-limiting examples.

EXAMPLES

Figure 9:
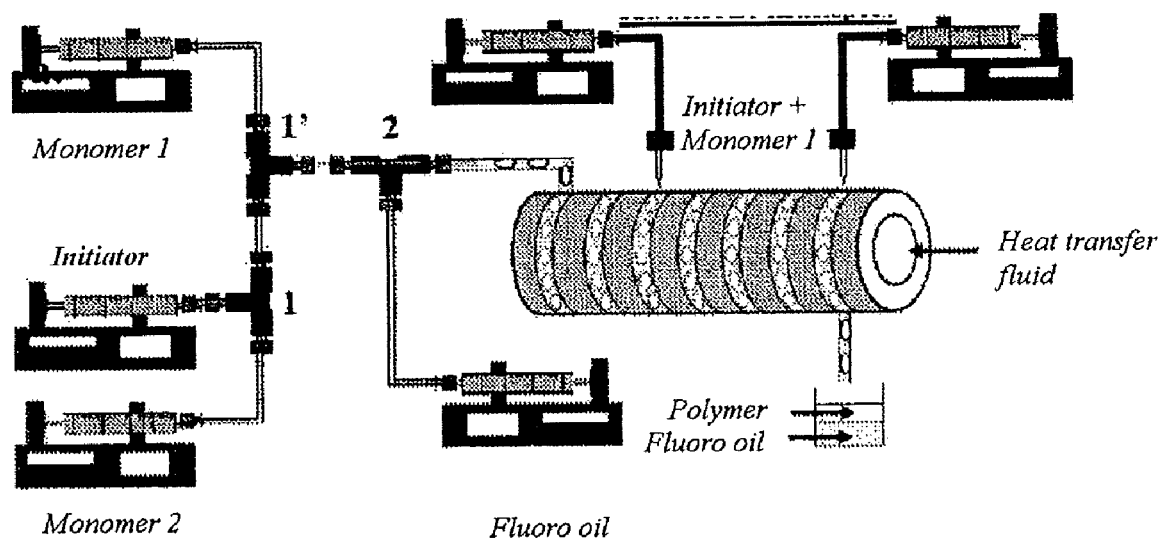
FIG. 9 is a view of the device used for carrying out the example.

A copolymer of acrylic acid (AA—Monomer 1) and of DADMAC (Monomer 2) was prepared using the device from FIG. 9, comprising. A fluoro oil was used as a carrier phase. The monomer 2 was mixed with sodium persulfate (initiator). This mixture is mixed with the monomer 1, to obtain a reaction mixture of given solids content. Plugs of the reaction medium were formed, separated by the fluoro oil (volume ratio of 1/1).

Flow of the plugs took place in a flexible tube arranged in a spiral around a heat transfer fluid as shown in the context of FIG. 5. In certain embodiments, a solution of monomer 1 and/or of initiator was injected using intermediate branch connections (at 1/3 and at 2/3 of the length of the tube). The flexible tube was made of PTFE, its internal diameter was 1.6 nm, its length was 4.8 m, and it was wound in 32 turns.

The conversion of the monomers was analyzed by RAMAN spectroscopy. The average molecular weights were also analyzed by chromatography.

Several experiments were carried out, having constant final monomer ratios.

Experiment 1:
  no branch connection;
  temperature of the heat transfer fluid: 90° C.;
  solids content: 54% by weight;
  residence time: 180 minutes;
  weight-average molecular weight: 1236000 g/mol;
  number-average molecular weight: 404000 g/mol;
  polydispersity index: 3.0; and
  conversion: 90%.

By way of indication, the data for a commercial polymer produced from the same relative amounts of monomers and of initiator in a conventional jacketed reactor are the following:
  solids content: 20% by weight;
  weight-average molecular weight: 282000 g/mol;
  number-average molecular weight: 48000 g/mol;
  polydispersity index: 5.9;
  conversion: 100%.

Experiment 2
  Introduction into the tube of 2/3 of the total amount of monomer 1+100% of the total amount of monomer 2+50% of the total amount of initiator, then 1st branch connection with introduction of 1/6 of the total amount of monomer 1+25% of the total amount of initiator, then 2nd branch connection with introduction of 1/6 of the total amount of monomer 1+25% of the total amount of initiator;
  temperature of the heat transfer fluid: 90° C.;
  solids content: 18.4% by weight;
  residence time: 180 minutes;
  weight-average molecular weight: 340000 g/mol;
  number-average molecular weight: 120000 g/mol;
  polydispersity index: 2.9; and
  conversion: 85%.

Experiment 3
A dishwasher formulation comprising, as additive, the commercial copolymer and another formulation comprising a copolymer prepared in example 2 were produced. Cleaning cycles for cleaning the dishes were carried out in the machine using these formulations.

The commercial polymer provided an interesting property of formation of film on the dishes. With the copolymer produced during experiment 2, this property was improved.

The invention claimed is:

1. A process comprising a preparation of polymer, in which a polymerization reaction medium is made to flow in a tubular flow member, known as a downstream tubular flow member, said medium being continuous or being composed of a succession of plugs in a carrier phase (P), wherein said polymer is formed in said reaction medium in said tubular flow member and optionally one of the following operations:
  at least one analysis of the reaction medium is carried out and at least one physical and/or chemical conversion feature of the polymer and/or of the polymerization is deduced therefrom;
  the reaction medium is recovered, the polymer is optionally isolated and used; and/or
  the polymer is tested.

2. The process as claimed in claim 1, wherein the polymerization reaction medium is formed from at least two components and these two components are circulated in at least two upstream tubular flow members, which open into the downstream tubular flow member.

3. The process as claimed in claim 2, wherein the reaction medium comprises at least three components, each of which flows into a corresponding upstream member.

4. The process as claimed in claim 3, wherein the reaction medium comprises at least one adjuvant for the conversion.

5. The process as claimed in claim 3, wherein at least three upstream tubular flow members are provided, at least two first upstream members being placed side by side within a peripheral upstream tubular flow member.

6. The process as claimed in claim 1, wherein the or each tubular flow member has an equivalent diameter between 10 micrometers and 50 mm.

7. The process as claimed in claim 2, wherein said at least two components are mixed in a mixing zone substantially at the same time as these components are brought into contact with the carrier phase, in a contacting zone substantially merged with the mixing zone.

8. The process as claimed in claim 2, wherein said at least two upstream flow members and the downstream flow member are concentric.

9. The process as claimed in claim 7, wherein the contacting zone is located immediately downstream of an overlap zone between the downstream flow member and a peripheral upstream flow member.

10. The process as claimed in claim 1, wherein the reaction medium or the isolated polymer is recovered, then it is used in an application.

11. The process as claimed in claim 1, wherein the polymer is tested.

12. The process as claimed in claim 1, wherein at least one analysis is carried out according to the following procedure:
the conversion that takes place in the reaction medium is stopped, especially by means of a quench, and at least one off-line analysis is carried out.

13. The process as claimed in claim 1, wherein a beam from an analysis unit, is pointed toward one zone of the downstream tubular flow member in which the polymerization continues to take place.

14. The process as claimed in claim 13, wherein the beam is pointed toward one and the same location of the downstream tubular flow member, and an analysis of several plugs that flow successively past said location is carried out.

15. The process as claimed in claim 1, wherein at least one part of the downstream flow member is placed in a member for maintaining at a given temperature.

16. The process as claimed in claim 1, wherein the process immobilizes, in the downstream flow member, at least some plugs, which enables the conversion to be followed without displacement of these plugs, then these plugs are again made to flow in this downstream tubular member after observation of this latent period.

17. The process as claimed in claim 1, wherein a primary reaction medium, comprising a first monomer and a polymerization initiator, is made to flow in the tubular flow member, and added to the primary reaction medium, is at least one other component, so as to form a modified reaction medium.

18. The process as claimed in claim 1, wherein the reaction medium, is made to flow in the downstream tubular flow member at a throughput between 1 ml/h and 1000 ml/h.

19. The process as claimed in claim 1, wherein the length of the downstream tubular flow member is between 50 cm and 10 m.

20. The process as claimed in claim 1, wherein the feature that is deduced is a rate of progress of the polymerization.

21. The process as claimed in claim 1, wherein the composition of several plugs and/or the temperature of a maintaining member is controlled by computer means, and/or results of various analyses are acquired by said computer means.

22. The process as claimed in claim 1, wherein at least one of said tubular flow members is flexible.

23. The process as claimed in claim 1, wherein the polymerization reaction medium is a radical polymerization reaction medium.

24. The process as claimed in claim 1, wherein the at least one analysis of the reaction medium is an analysis of at least one plug.

25. The process as claimed in claim 6, wherein each tubular flow member has an equivalent diameter between 50 micrometers and 5 mm.

26. The process as claimed in claim 6, wherein each tubular flow member has an equivalent diameter between 100 micrometers and 1 mm.

27. The process as claimed in claim 13, wherein the analysis unit is a RAMAN unit.

28. The process as claimed in claim 17, wherein the primary reaction medium is comprised of primary plugs.

29. The process as claimed in claim 18, wherein the at least one additional component is added to each primary plug.

30. The process as defined in claim 17, wherein the at least one addition component is another monomer and/or a supplementary amount of an initiator.

31. The process as claimed in claim 17, wherein the modified reaction medium is comprised of modified plugs.

32. The process as claimed in claim 31, wherein the modified reaction medium is a definitive reaction medium comprising definitive plugs.

33. The process as claimed in claim 18, wherein the reaction medium is comprised of plugs.

34. The process as claimed in claim 18, wherein the throughput is between 5 ml/h and 100 ml/h.

35. The process as claimed in claim 19, wherein the length of the downstream tubular flow member is between 1 m and 4m.

36. The process as claimed in claim 4, wherein the at least one adjuvant is a catalyst or an initiator.

* * * * *